United States Patent [19]

Saunders

[11] Patent Number: 5,205,815
[45] Date of Patent: Apr. 27, 1993

[54] ATHLETIC BACK SUPPORT APPARATUS

[76] Inventor: Harold D. Saunders, 9840 Purgatory Rd., Eden Prairie, Minn. 55347

[21] Appl. No.: 719,267

[22] Filed: Jun. 21, 1991

[51] Int. Cl.$^5$ .................... A61F 5/00; H04B 17/02
[52] U.S. Cl. .................................. 602/19; 450/150
[58] Field of Search ............... 602/19; 450/150, 155, 450/89, 95, 119, 120; 128/100.1, 101.1

[56] References Cited

U.S. PATENT DOCUMENTS

| | | | |
|---|---|---|---|
| 1,599,688 | 9/1926 | Sullivan | 450/95 |
| 2,088,302 | 7/1937 | McKeever . | |
| 2,232,246 | 2/1941 | Klein . | |
| 2,249,198 | 7/1941 | Carter . | |
| 2,481,396 | 9/1949 | Cohen | 450/95 |
| 2,553,353 | 5/1951 | Binder et al. . | |
| 2,641,258 | 6/1953 | Rutledge . | |
| 2,910,984 | 11/1959 | Yeakey et al. . | |
| 3,029,814 | 4/1962 | Kravitz . | |
| 3,141,457 | 7/1964 | Davidson | 128/101.1 X |
| 3,234,937 | 2/1966 | Nelkin . | |
| 3,441,027 | 4/1969 | Lehman | 602/19 X |
| 3,526,229 | 9/1970 | Blair | 450/155 X |
| 3,756,247 | 9/1973 | Hand | 450/155 X |
| 4,400,832 | 8/1983 | Kinder | 128/100.1 X |
| 4,475,543 | 10/1984 | Brooks et al. | 602/19 |
| 5,040,524 | 8/1991 | Votel et al. | 602/19 |

OTHER PUBLICATIONS

1991 Catalog of "Saunders Therapy Products"—pp. 26, 27, 28 and 35 and cover sheet.
News Release for Dyna-Life TM Active Support Belt published on p. 59 of "Physical Therapy Products", Mar. 1991.
*Managing Lower Back Pain, 2d Ed.,* W. H. Kirkaldy-Willis, Churchill Livingstone, 1988; pp. 297-303.
*Camp Therapy Products Price List,* Camp International, Inc., Jun. 1988.

*Primary Examiner*—Richard J. Apley
*Assistant Examiner*—Linda C. M. Dvorak
*Attorney, Agent, or Firm*—Merchant, Gould, Smith, Edell, Welter & Schmidt

[57] ABSTRACT

A back support orthosis garment particularly applicable for vigorous athletic activities is disclosed. A lumbosacral support designed to partially immobilize all or a portion of the lumbar vertebrae, is maintained in a predetermined aligned position relative to the wearer's spine by means of a compression-type short/pant that also provides graduated compressive support to the thigh and groin area muscles of the wearer. The compression-type short and lumbosacral support structures are integrally designed in a single garment that is comfortably worn and which maintains the aligned position of the lumbosacral support relative to the spine, regardless of the degree of movement of the wearer.

18 Claims, 6 Drawing Sheets

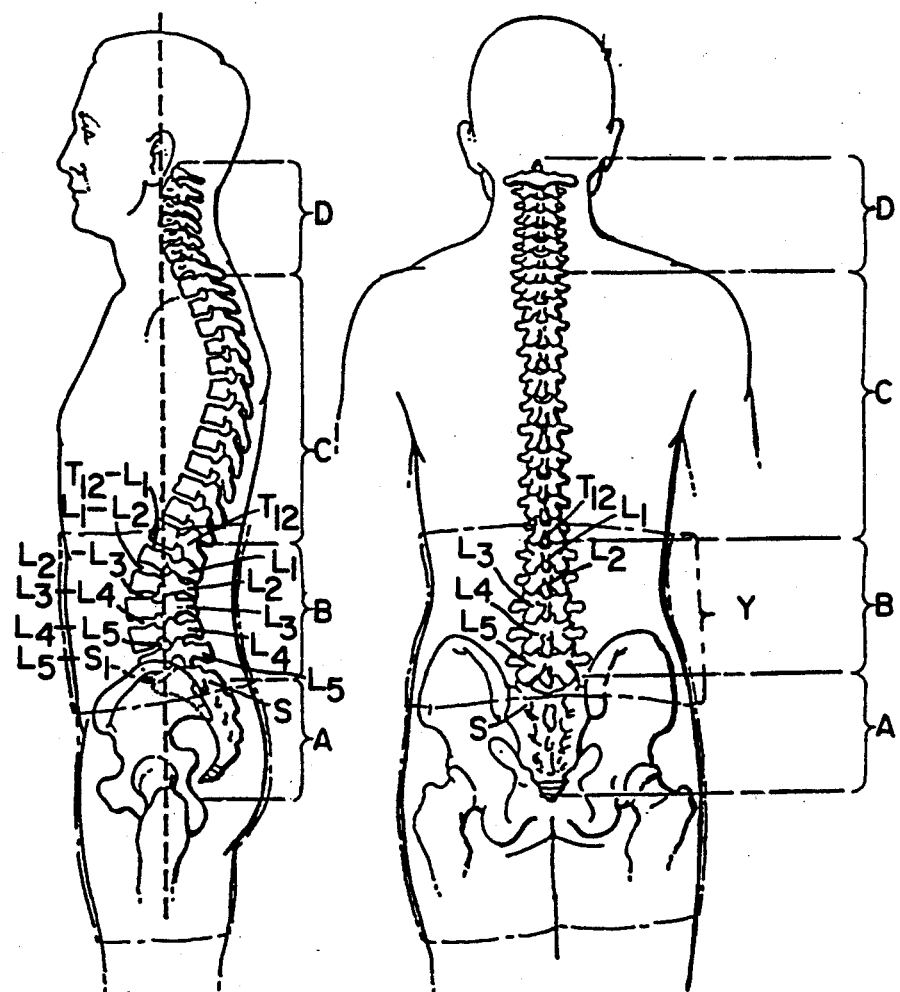
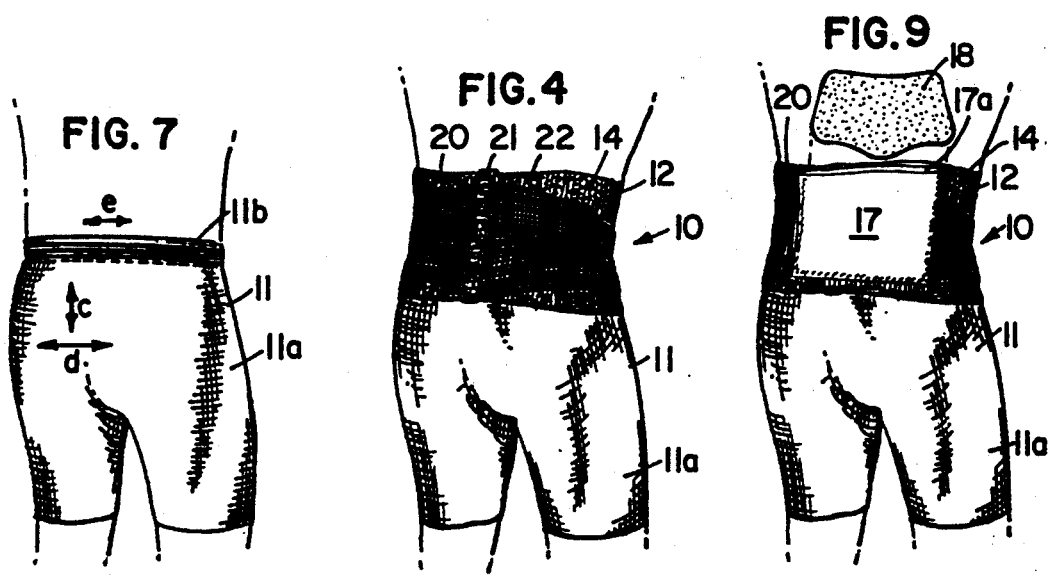

ATHLETIC BACK SUPPORT APPARATUS

BACKGROUND OF THE INVENTION

1. Field of the Invention

This invention relates generally to orthopedic garments, and more specifically to a lumbosacral orthosis garment uniquely designed for athletes or active industrial workers.

2. Description of the Art

Lower back disorders and the pain associated therewith have become epidemic in today's society. Such disorders are typically caused by a combination of poor posture, faulty body mechanics, stressful living and working habits, loss of flexibility and a general decline in physical fitness. In general, the best non-surgical management techniques for such disorders include proper strengthening exercises, treatment and rest, and back-care education. However, there are many instances in which orthopedic orthoses in the form of lumbosacral braces, supports and the like can be effectively used to supplement such management techniques or to help prevent injury or reinjury to the lower back. Such orthoses are particularly useful in reducing mobility of the spine joints so as to reduce the amount of intervertebrae bending and intervertebrae torsion in the regions where the garments are applied and also function to lessen the average axial loading and bending loading on the spine, thereby, avoiding or reducing strain and aggravation to the spine during physical activity. Such orthoses (typically referred to as "backbrace") devices are also helpful in reminding the wearer of the fact that an injury has taken place and that he should not make sudden motions that will override the protective mechanisms of his body, and/or to provide definitive protection against those kinds of rapid dynamic motion that occur during strenuous athletic or industrial activity.

The need for such orthopedic orthoses devices is particularly acute for those involved in strenuous athletic or industrial work activities which place abnormal stress and strain on the spine. In performing their required functions, such individuals do not always have the opportunity to observe desired back safety and protection guidelines and can often use the additional support and protection provided by an orthopedic orthosis.

A number of styles of lower back support orthoses have been known in the art. Such devices, which are typically configured to provide sacroiliac support or support for the lumbar spine region, have generally been effective for use by those who are not involved in any physical activity involving rapid movement. However, for those activities involving strenuous motion including stretching, twisting or jumping, which may for example be experienced by basketball players, hockey players or golfers, such standard orthoses devices have a tendency to migrate or ride up on the body of the wearer. To be effective in providing relief or support to the lower spine, such devices necessarily partially encircle the pelvis and hips and at least partially overlie the upper buttocks region of the wearer, which naturally tends to urge the orthosis upward on the body during physical activity. On an active wearer, it does not take long for such orthosis to rapidly migrate upward on the body, thereby decreasing its effectiveness and becoming very uncomfortable for the wearer. In such instances, the orthosis becomes more of an impediment to the wearer than an aid.

Efforts have been made in the art to maintain the desired position of the orthosis on the body. Crotch, groin and leg straps secured to the lower edges of the orthosis have been used in an attempt to keep the orthosis from riding up on the wearer's body. Such structures, however, have been largely unacceptable to active wearers such as athletes, due to the discomfort and irritation caused by the pressures and chafing of such straps. Besides the desirability for lower back support, active athletes often also have a need for support of their upper thighs (i.e., hamstring and quadricep muscles), their abdomen muscles and their groin area muscles. While earlier techniques typically required individual support structures for each such set of muscles, modern "compression" shorts or liners constructed of nylon/spandex ® or cotton/poly/lycra ® fabrics have been found to be effective in simultaneously providing graduated compression and support to the hamstring, quadricep, groin area and abdominal muscles—while yielding superior flexibility and comfort over prior art individual support techniques. Heretofore, however, no attempt has been made to combine the support features offered by such compression shorts with those of an orthopedic lumbar support orthosis.

This invention provides such combination, in a manner which enables an active athlete or individual to comfortably wear a lumbar support orthosis which stays in place during strenuous active movement and which simultaneously provides desired support to the upper thigh, groin area and abdominal muscles.

SUMMARY OF THE INVENTION

The present invention provides a highly effective versatile and comfortable combination lumbar support orthosis and compression short/pant garment for active individuals such as athletes and industrial users. According to one aspect of the invention, there is provided a garment for providing back support to the spine of a wearer, comprising a compression-type short, and a lumbosacral support operatively connected with the short, wherein said short maintains the vertical position of the lumbosacral support relative to the spine of the wearer during active movement of the wearer. The compression-type short preferably comprises elastic material which is elastic in the directions of two mutually orthogonal axes of the material. According to one aspect of the invention, the compression-type short includes leg portions which are designed and configured to extend at least partially down the thigh region of the wearer, to support the thigh and groin area muscles. According to another aspect of the invention, the compression-type short is configured as a brief, and may or may not include an access fly.

The lumbosacral support portion of the garment may include an elastic support band designed to circumferentially extend around the body of the wearer and having at least a portion thereof configured to supportively engage the lumbosacral spine region of the wearer's body. According to one embodiment of the invention, the elastic support band may include a plurality of interconnected elastic bands which collectively perform the support function and readily conform to the contours of the wearer's body. The lumbosacral support member preferably includes one or more stay members and means, which may be in the form of adjustable strap members, for applying pressure through the stay members to the lumbosacral spine region of the user. A garment constructed according to the principles of this invention enables a lumbosacral support structure to be accurately aligned with the user's body for maximizing the desired degree of immobilization of the lumbar vertebrae, and for anchoring the support member to the wearer's pelvis regardless of the degree of physical movement of the wearer. The garment is constructed of appropriate materials and is designed so as to maximize comfort to the wearer during vigorous physical activity—while achieving its functional purposes.

According to another aspect of the invention, there is provided such a combination lumbosacral support and compression-type short garment with a discontinuous elastic support band which can be adjustably fastened to a desired degree of compression by appropriate fastening means. Such a device is particularly suitable for wearers having enlarged abdomens or for such wearers which require additional abdominal support.

While the present invention will be described with respect to its use by athletes, it will be understood that the invention is not to be so limited, but can be used by any individual requiring or desiring the combined support features offered by this invention. Further, while the present invention will be described with respect to particular brands and types of materials, it will be understood by those skilled in the art, that the invention is not to be limited by any particular type or brand of material, but that such materials are used for descriptive purposes only. Further, while the invention will be described with regard to a particular style of compression short/pant and with regard to such a compression short/pant having a particular leg configuration, that the invention is not to be so limited, but applies equally well to shorts/pants of various styles and configurations and to those having, for example, longer or shorter leg segments Further, while the invention will be described with respect to a particular style of lumbar support orthosis using a particular number and style and configuration of vertical stay members, it will be understood by those skilled in the art that the invention is not limited, other than as claimed, to the particulars of the orthosis structures described in the preferred embodiments. Further, while the present invention will be described with respect to an orthosis garment which has a primary function of providing support for the lumbar spine region, it will be understood that additional support structures such as those specifically developed for a sacroiliac support could be incorporated within the overall structure of the garment. These and other modifications and applications of the invention will become apparent to those skilled in the art in light of the following description of preferred embodiments of this invention.

BRIEF DESCRIPTION OF THE DRAWING

Referring to the Drawing, wherein like numerals represent like parts throughout the several views:

FIG. 1 is a diagrammatic side view representation of a human body illustrating the four defined physiological curve regions of the spine;

FIG. 2 is a diagrammatic representation of the human body of FIG. 1, illustrated from a back or posterior view;

FIG. 4 is a back perspective view of the lumbar support orthosis garment of FIG. 3;

FIG. 7 is a view illustrating the compression short/pant portion only of the lumbar support orthosis garment of FIG. 4;

FIG. 9 is a back perspective view with portions thereof broken away of the lumbar support orthosis garment of FIG. 4 modified to include an insertable thermoform moldable insert.

DETAILED DESCRIPTION OF THE INVENTION

Diagrammatic views of a human body, generally illustrating the spinal column and its orientation and position relative to the sacrum and ilium of the sacroiliac region of the body are illustrated in FIGS. 1 and 2. FIGS. 1 and 2 will be used to facilitate describing placement of the orthosis garment of this invention relative to the human body and to the vertebrae of the spinal column. It is not the intent of this specification to describe the operation or medical disorders associated with the spinal column, it being understood that those skilled in the art are knowledgeable in such matters and/or need not be knowledgeable in the physiological peculiarities of the human body in order to effectively use the present invention. For a more detailed description, however, of the physiological anatomy of the spinal column and of the various musculoskeletal disorders associated therewith, the reader is referred to the text *Evaluation, Treatment and Prevention of Musculoskeletal Disorders* by H. Duane Saunders, Educational Opportunities, 1985. To the extent that any of the materials of my above-identified book are relevant to an understanding of the art, or of the use or applicability of my invention to providing support for the spinal vertebrae of the human body, they are herein incorporated by reference.

In general, with reference to FIGS. 1 and 2, the spine has four curved areas generally designated at "A, B, C and D". The sacral curved region "A" comprising the fused bones of the sacrum is convex posteriorly. The lumbar region of the spine, generally designated at "B" is concave posteriorly. The thoracic region of the spine "C" is convex posteriorly. The cervical region of the spine, generally designated at "D" is concave posteriorly. This invention focuses primarily in providing support for those portions "A" and "B" of the spinal column referred to as the lumbosacral region. The lumbar region generally includes five vertebrae generally labeled "$L_1$" through "$L_5$" in FIGS. 1 and 2. The $L_5$ lowermost vertebrae of the lumbar region lies adjacent the sacrum "S" and is separated thereby by spinal joint labeled "$L_5$-$S_1$". The uppermost vertebrae "$L_1$" of the lumbar region lies adjacent to and is separated from the lowermost vertebrae "$T_{12}$" of the thoracic region by the joint labeled as "$T_{12}$-$L_1$". While there is some dispute as to the relative percentages of lumbar flexion/extension of the various joints in the lumbar region, most authorities agree that most of the flexion/extension takes place at the "$L_4$-$L_5$" and the "$L_5$-$S_1$" joints.

Figure 3:
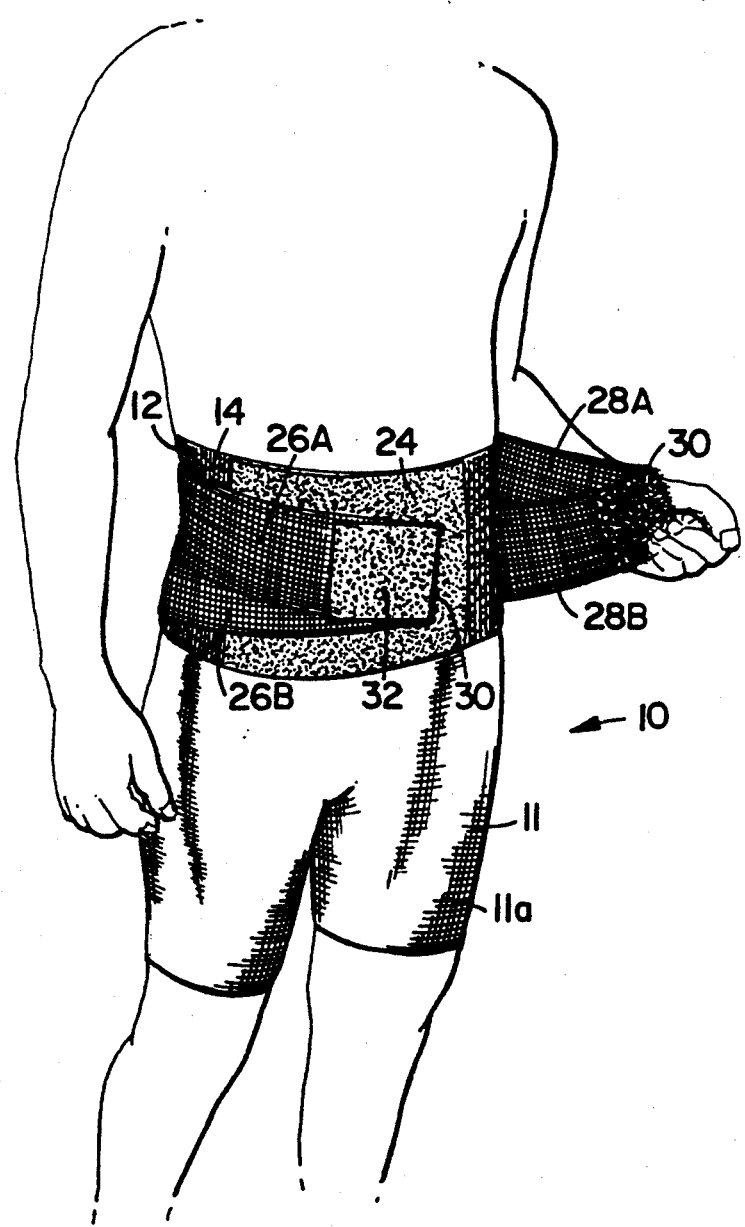
FIG. 3 is a front perspective view of a first embodiment of a lumbar support orthosis garment of the present invention illustrated as it would be operatively positioned on a human body.
Figure 3A:
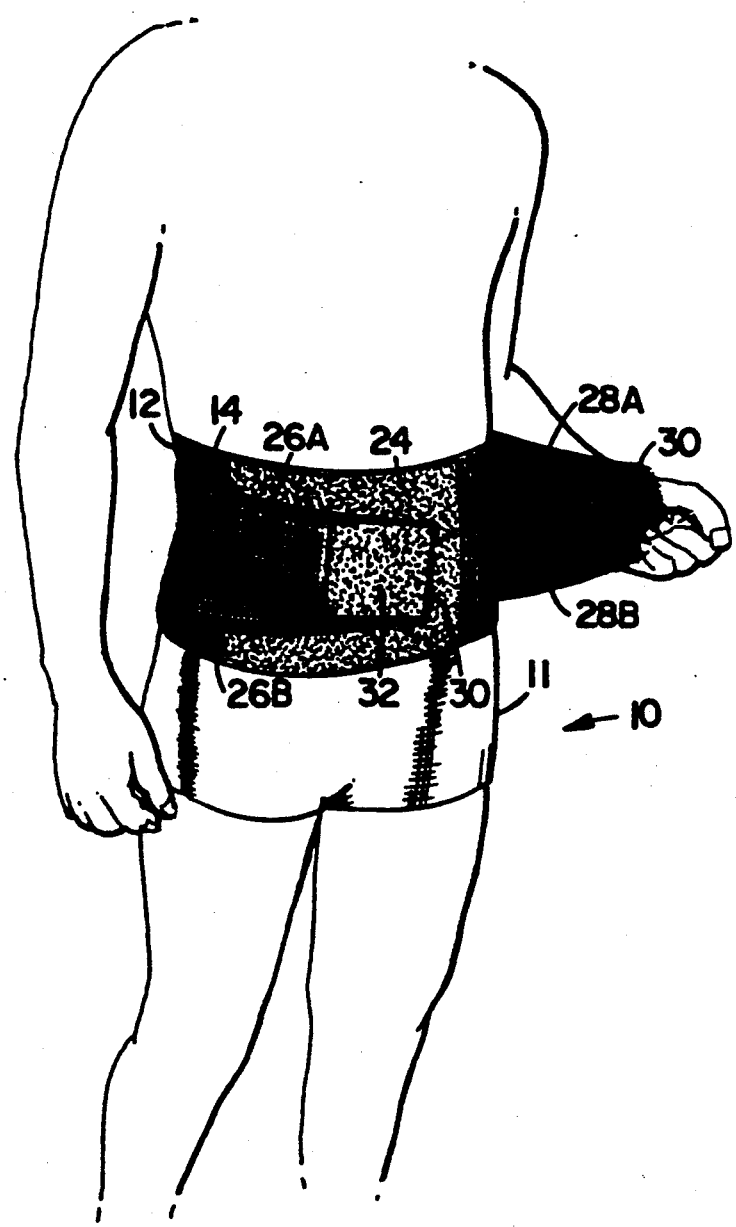
FIG. 3A is a front perspective view of an alternate lumbar support orthosis connected to a brief.

Referring to FIG. 3, a first embodiment of a lumbosacral support orthosis garment configured according to the principles of my invention is generally illustrated at 10. The garment 10 generally comprises the combination of a lower compression short/pant portion 11 to which is secured an upper lumbosacral support brace assembly portion 12. The compression short/pant portion 11 of the garment 10 is separately illustrated in FIG. 7 as it would appear positioned on a human body. The compression short/pant 11 generally comprises a short or pant-shaped lower portion 11a of light to medium weight elastic material appropriately stitched to form the short or pant configuration and having elasticity in both the warp and weft directions of the material, generally running in the directions of the arrows "c" and "d" of FIG. 7. The elastic material 11a may be of any appropriate type which provides the desired compressive support to the body, yet is comfortable to wear. Examples of materials which are suitable for the purpose include cotton/poly/lycra ® fabric and nylon/spandex ® material. Both offer the desired four-way stretch and provide graduated compression and support to the hamstring, quadricep, groin area and abdominal muscles encircled thereby. The pant-shaped portion 11a is secured near its upper end by a circumferential waistband 11b of elastic material which is elastic primarily only in the direction indicated by the arrow "e" in FIG. 7. In the preferred embodiment of the invention, the length of the leg portions of the compression pant portion 11a extends from the crotch area of the compression short to a midthigh position so as to give compressive support to both the hamstring and the quadricep muscles of the wearer. It will be understood from a more complete description of the invention, however, that the principles of the invention would apply equally well to a compression pant configuration having truncated leg portions which terminate adjacent the crotch area, typically, referred to as a "jockey-brief" configuration, as illustrated in FIG. 3A. Such configuration, while providing less support to the hamstring and quadricep muscles still provides support for the groin area muscles and accomplishes the purposes of maintaining the upper lumbosacral support brace assembly 12 in operative position during strenuous activity of the wearer.

Figure 5:
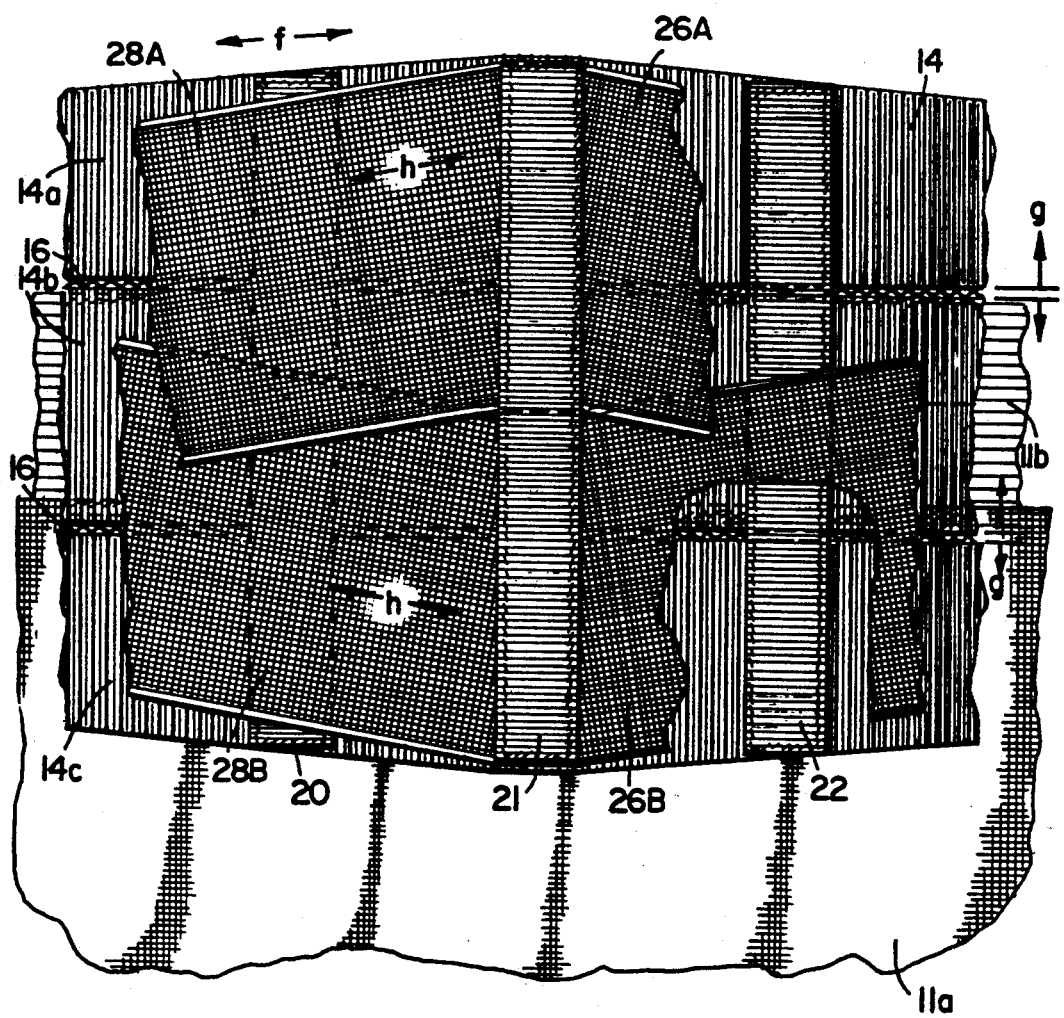
FIG. 5 is an enlarged fragmentary view, with sections thereof broken away of the back portion of the lumbar support orthosis garment of FIG. 4.
Figure 6:
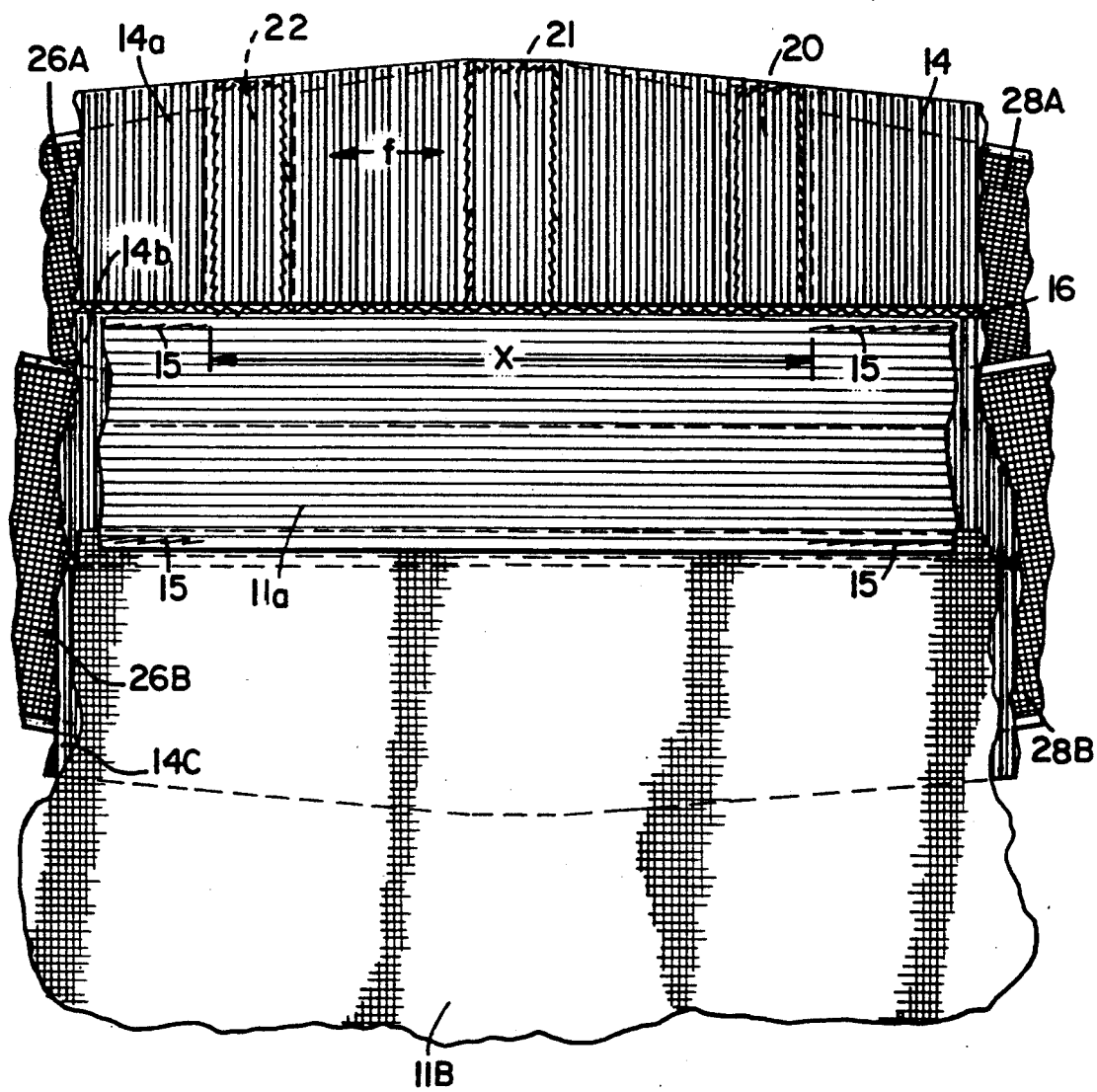
FIG. 6 is an enlarged fragmentary view of the lumbar support orthosis garment of FIG. 5, illustrated from the opposite (interior) side thereof.

The lumbosacral support brace assembly portion 12 of the orthosis garment 10 is illustrated in FIGS. 3–6. In the preferred embodiment illustrated, the support brace assembly 12 includes a circumferential support band 14. The support band 14 is circumferentially sized to encircle the body of the wearer and has a circumference slightly larger than that of the waistband 11b of the compression short/pant portion 11. The waistband 11b is circumferentially secured to the inner surface of the support band 14, as illustrated in FIGS. 5 and 6 by stitching 15 which circumferentially extends around the waistband 11b except for a length of the waistband 11b at the back of the compression short. In the preferred embodiment, that portion of the waistband not containing the circumferential stitching is illustrated in FIG. 6 at "x". In the preferred embodiment, the support band 14 is elastic, but it need not necessarily be made of elastic material.

As best illustrated in FIG. 5, the elastic circumferential support band 14 comprises, in the preferred embodiment, three individual support bands 14a, 14b and 14c, of equal circumferential length and circumferentially joined by cross-stitching 16 along their respective adjacent edges, to collectively comprise the support band 14. The material of the bands 14a, 14b and 14c is of relatively heavyweight elastic material with elasticity generally running only in the directions of the arrow "f". The cross-stitching 16 between the multiple bands 14a, 14b and 14c provides limited interband elasticity in the direction indicated by the arrows "g" to enable the multiple-band configuration to more readily conform to the body contours of the wearer. It will be understood by those skilled in the art, that the particular construction of the support band 14 is not to be limited to that herein described for the preferred embodiment. For example, while a multiple-band configuration has been illustrated, a single-band configuration could also be employed. Similarly, while a multiple-band configuration comprising three interconnected bands has been illustrated, any number of such bands or strips of material comprising a multiple-band configuration could be employed within the spirit and intent of this invention. In the preferred embodiment, the inner surfaces of the bands 14a, 14b and 14c are lined with a soft elastic surface to provide additional comfort to the wearer and to prevent irritation and chafing of the wearer's body as the support band 14 moves against the body in operative use. In the preferred embodiment, the soft elastic material is of a type sold under the HELANCA ® trademark.

The height or width of the support band 14 can vary, depending upon the size of the wearer. For an adult, the support band width or height is preferably between 8 and 12 inches. More important, however, than the numerical dimension is the relation of the support band height or width in relation to its operative position relative to the spine of the wearer. With reference to FIGS. 1 and 2, the support band height (illustrated in phantom at 14) should preferably be designed to extend on the wearer such that its lower edge extends to the sacrum and even more preferably to the middle of the sacrum, and such that its upper edge at least covers the first two joints ($L_4$-$L_5$ and $L_3$-$L_4$) of the lumbar region. More preferably still, the upper edge should extend so as to cover all five vertebrae and all of the intervening joints of the lumbar region, as illustrated by the dimension "y" in FIG. 2.

A plurality of flexible stay members 20, 21 and 22 are securely attached in generally vertical alignment in circumferentially spaced positions along the posterior portion of the support band 14. In the preferred embodiment illustrated, the central stay member 21 is operatively positioned for direct vertical alignment with the spinal column of the wearer, and the stay members 20 and 22 are configured so as to be vertically aligned slightly to either side of the spinal column. In the preferred embodiment, the "length" of the stay members generally correspond to the width or height of the support band 14. It will be understood by those skilled in the art, however, that there need not be an identical correspondence in such dimensions and that the number and relative spacing of such stay members is a matter of design choice. In general, the length of the stay members 20–22 and their relative operative position with respect to the vertebrae of the spinal column of the wearer are generally the same as previously discussed with respect to the width or height dimensions of the support band 14 and its positioning relative to the spinal column of the wearer. The stay members may be of any appropriate semirigid material such as plastic or metal, well known to those skilled in the art. In the preferred embodiment, the stays are preferably made from hardened, galvanized spring steel round wire which is coiled and flattened, and is generally referred to in the trade as "spiral boning". Such material provides support rigidity for partially immobilizing the spinal column vertebrae, yet can be flexed, when placed under pressure, to conform to the body contours of the wearer, as illustrated in FIG. 4. Referring to FIG. 6, in the preferred embodiment, the "x" dimension portion of the waistband 11b over which the waistband 11b and the support band 14 are not stitched together corresponds generally to the spacing between the outermost stay members 20 and 22. This configuration enables the stay members to be pulled into snug engagement with the wearer's body adjacent the spinal column, without imparting corresponding circumferential tension to the waistband portion 11b of the compression short/pant 11 of a nature that would tend to cause binding or gathering of the waistband.

Referring to FIG. 3, a panel of fastener material 24 is secured to the front portion of the support band 14. In the preferred embodiment, the fastener material 24 comprises a sheet of "looped" material suitable for engagement by a corresponding hooked fastener, both sold under the Velcro ® trademark. A pair of tapered side pull elastic adjustable strap members 26 and 28 are each secured to the support band 14 at its posterior end and in alignment with the centrally positioned stay member 21. Each of the tapered side pull members comprises, in the preferred embodiment, a pair of elastic straps 26A, 26B and 28A, 28B respectively, each having one end thereof secured to the posterior of the support band 14 at the central stay member 21. At their point of connection to the support band 14, the respective pairs of material comprising the straps 26 and 28 are spaced relative to one another so as to extend the full width or height of the support band 14. The elastic side pull members 26 and 28 are constructed of relatively stiff elastic material which is elastic primarily only in the direction as indicated by the arrows "h" in FIG. 5. The elastic pairs comprising the side pull straps 26 and 28 taper from their secured ends toward their unsecured ends and overlap one another (as illustrated in FIG. 3), each terminating at a Velcro ® hook fastener member 30. In FIG. 3, the tapered end of the side pull strap 26 is illustrated as secured by its Velcro ® hook fastener 30 to the looped fastener panel 24. The side pull strap 26 also includes a smaller panel of looped fastener material 32 secured to its outer surface. The Velcro ® hook fastener material of the side pull strap 28 can be secured either to the larger panel 24 of looped fastener material, to the smaller panel 32 of looped fastener material, or to both, as is obvious from the illustration of FIG. 3.

To place the lumbar support orthosis garment 10 in operative position, the wearer unfastens the side pull adjustable straps 26 and 28, and pulls the assembly over his legs and up to his waist area just as he would a pair of shorts or trousers. It is contemplated that the compression short/pant portion 11 would be manufactured in a number of different sizes such that waistband 11b of the compression short member is aligned generally with the waist of the wearer. In such position, the support band 14 and its secured stay members 20, 21 and 22 are properly aligned with the wearer's spinal column so as to support the lumbosacral vertebrae and joints of the wearer as hereinbefore described. The stays 20, 21 and 22 are pulled into firm engagement with the wearer's back and are adjusted to the desired pressure by first pulling and securing the side pull strap 26 in the position as illustrated in FIG. 3, and by subsequently pulling and securing the side pull strap 28 and its hook fastener 30 into overlapping engagement with the loop fastener member portion 32 and the primary loop fastener panel portion 24. When thus secured, the stay members 20, 21, and 22, in combination with the side pull straps and the underlying circumferential support band 14 serve to partially immobilize the motion of the lumbosacral vertebrae, thereby reducing the amount of interspine bending and interspine torsion in such regions and decreasing the pressures acting on the intervertebrae disks. The combined forces of the elastic circumferential support band 14 and the elastic side pull straps also provide abdominal support, and the elastic nature of the compression short/pant 11 provides graduated compression support for the groin area, abdominal, hamstring and quadricep muscles. Due to the unitary structure of the compression short/pant portion 11 and the lumbosacral support brace assembly portion 12 of the composite garment 10, the support brace assembly portion 12 is securely fixed at the predetermined desired support position on the wearer regardless of the activity level or extent of movement of the wearer. Further, due to the distributed nature of the forces applied by the body of the wearer through the compression short/pant portion 11 of the garment and due to the nature of the soft lining material of the circumferential support band 14, comfort to the wearer throughout his active movements, is maximized such that the garment 10 performs its intended functions without undue discomfort or irritation to the wearer. The adjustable nature of the side pull straps enables the degree of immobilization support provided to the spinal column and the amount of support provided to the abdomen to be varied according to the needs of the wearer.

A number of additional features can be added, and changes made to the above-described embodiment of the invention, by those skilled in the art. An example of one such additional feature is diagrammatically illustrated in FIG. 9. Referring thereto, the support brace assembly 12 has been modified to include a pocket or pouch 17 attached to the "inside" surface of the support band 14. Alternatively, such pouch could be integrally formed within the support band. The pocket 17 is oriented so as to address the lumbosacral region of the wearer's spine and is positioned between the support band 14 and the waist-band 11b. The pocket 17 has an upper access port 17a that may accommodate appropriate closure means and is sized and configured to cooperatively accept a thermoform moldable insert member 18. Insert 18 is illustrated in FIG. 9, removed from the pocket 17. Such insert members, well known in the art, generally have an inner core of thermoplastic material having a peripheral shape that conforms to the general contour of the lower back, and an outer coating of foam padding or other material to enhance wearer comfort. Upon application of heat, the thermoplastic of the insert becomes pliable and can be molded to the desired orthosis shape that uniquely "fits" the lumbosacral back region of the wearer. Upon cooling, the insert retains its molded shape. While such inserts can assume any desired size and shape, in the preferred embodiment illustrated, the insert has a "width" that spans virtually the entire back area of the wearer and a "height" that is approximately the same as that of the support band 14.

Figure 8:
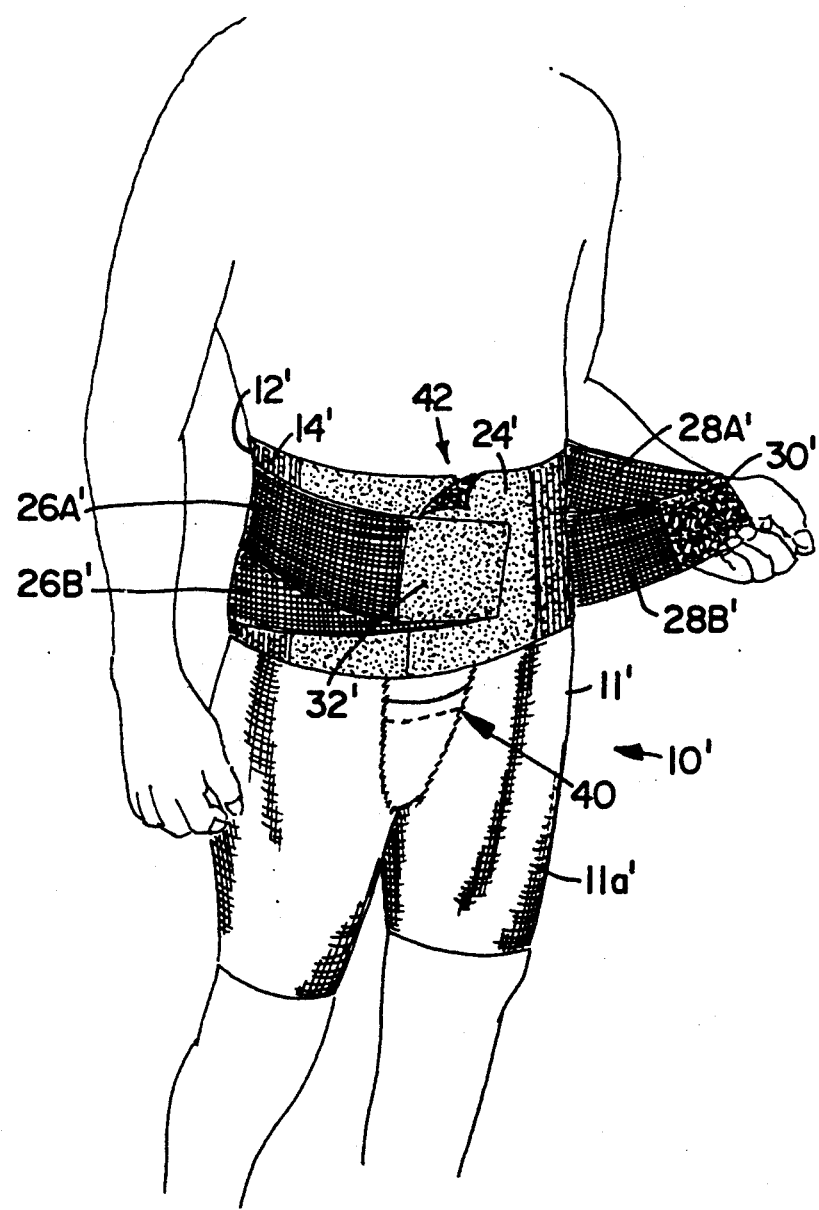
FIG. 8 is a front perspective view of a second embodiment of a lumbar support orthosis garment of the present invention, illustrated as it would be operatively positioned on a human body.

A second embodiment of a lumbar support orthosis garment illustrating additional features that can be readily incorporated into the garment, is illustrated in FIG. 8. The same numerical terminology for similar garment portions has been maintained between the first and second embodiments of the orthosis garments, with the addition of a "prime" designation for the second embodiment numbers.

Referring to FIG. 8, the second embodiment of a lumbar support orthosis garment 10' is virtually identical to that of the first embodiment with the addition of a fly configuration generally designated at 40 in the compression short/pant portion 11' of the garment 10'. In the preferred embodiment, the fly portion 40 is of a type well known in the art, generally comprising a horizontal access port through the elastic material 11a' of the compression short/pant portion 11' and disposed at a position such that the groin support properties of the compression short/pant are retained. While a horizontal fly configuration has been illustrated, it will be understood by those skilled in the art that other fly configurations could equally well be used. An additional feature of the orthosis garment 10' of the second embodiment is that the elastic support band 14' is vertically split along the front portion thereof as generally illustrated at 42 in FIG. 8, the ends of which are appropriately detachably secured to one another by appropriate fastener material such as Velcro ® hook and looped material or the like. Once secured, the split support band 14' serves the same function as its counterpart support band 14 in the first embodiment of the invention. The advantage of the second embodiment configuration having a split support band 14' is that such a structure may enable easier application by a wearer having a fairly large abdomen, and can provide extra and adjustable abdominal support for such person independent of the adjustable support pressure applied to the lumbosacral region of the wearer.

It will be appreciated that the lumbosacral support orthosis garment of the present invention provides the combined benefits of a compression short/pant with that of a lumbosacral support. This invention not only provides such a combination feature, but enables the lumbosacral support to be essentially "anchored" to the wearer's pelvis during active movement of the wearer. The present invention provides for accurate alignment, adjustment and balance of the lumbar support portions of the garment.

Other modifications of the invention will be apparent to those skilled in the art in view of the foregoing descriptions. These descriptions are intended to provide specific examples of embodiments which clearly disclose the present invention. Accordingly, the invention is not limited to the described embodiments or to the use of specific elements, dimensions, materials or configurations contained therein. All alternative modifications and variations of the present invention which fall within the spirit and broad scope of the appended claims are covered.

I claim:

1. A garment for providing back support to the spine of a wearer, comprising:
   (a) a compression short having elastic means for conforming said compression short tightly to the pelvis, groin area, and lower abdominal muscles of the user; and
   (b) a lumbosacral support having means for engaging the spine from approximately the sacrum to at least the $L_3$ lumbar vertebrae operatively connected with said compression short, wherein said compression short maintains the vertical position of said lumbosacral support relative to the spine of the wearer during active movement of the wearer.

2. The garment of claim 1, wherein said compression short comprises elastic material, elastic in the directions of two mutually orthogonal axes, and wherein said short includes leg portions designed and configured to extend at least partially down the thigh regions of a wearer.

3. The garment of claim 1, wherein said compression short is designed and configured as a brief.

4. The garment of claim 3, wherein said compression short comprises elastic material, elastic in the directions of two mutually orthogonal axes.

5. The garment of claim 1, wherein said short includes an access fly through one surface of the compression short.

6. The garment as recited in claim 1, wherein said lumbosacral support includes a support band operatively connected with said short and configured to circumferentially extend around the body of the wearer, said support band having at least a portion thereof configured to supportively engage the lumbosacral spine region of the wearer's body.

7. The garment as recited in claim 6, wherein said support band comprises elastic material, elastic primarily only in the circumferential direction of the band.

8. The garment as recited in claim 7, wherein said elastic support band comprises a plurality of circumferential bands coaxially aligned with one another and having adjacent edges respectively thereof interconnected to provide a composite said support band that conforms to the contours of the wearer's body.

9. The garment of claim 1, wherein said lumbosacral support includes one or more semi-flexible stay members, and means for operatively applying pressure through said one or more stay members to the lumbosacral spine region of the wearer.

10. The garment of claim 9, further including means for orienting said one or more stay members generally parallel to the axis of the lumbar vertebrae of a wearer of said garment.

11. The garment of claim 9, wherein said one or more stay members are sized and configured to engage the wearer's back from approximately the sacrum to at least the $L_3$ lumbar vertebrae of the wearer's spine.

12. The garment of claim 9, wherein said pressure applying means comprises one or more adjustable strap members for selectively varying the pressure applied to the wearer's back through said one or more stay members.

13. The garment of claim 12, wherein said garment defines a front portion and a back portion, wherein said one or more stay members are operatively disposed near said back portion of the garment, and further including means disposed near said front portion of the garment for adjustably fastening said strap members at said front portion.

14. The garment of claim 6, wherein said support band is circumferentially discontinuous, and further including fastener means for adjustably closing the support band discontinuity.

15. The garment of claim 1, wherein said lumbosacral support includes means for retainably holding a formable insert brace member that can be preformed to uniquely conform to the shape of a wearer's back in the lumbosacral region.

16. The garment of claim 15, further including an insert brace member securable by said holding means and of a type that is formable to uniquely conform to the shape of a wearer's back in the lumbosacral region.

17. A lumbosacral orthosis support garment for athletes, comprising:
   (a) a lumbosacral support member having means for engaging the spine from approximately the sacrum to at least the $L_3$ lumbar vertebrae arranged and configured so as to apply support pressure to the body of a wearer to at least partially immobilize movement of one or more of the lumbar vertebrae of the wearer's spinal column; and
   (b) a pant configuration having elastic means for conforming said pant configuration tightly to the pelvis, groin area, and lower abdominal muscles of the user, said pant configuration being operatively connected with said support member for anchoring said support member to the pelvis of the wearer regardless of the degree of physical movement of the wearer.

18. A unitized back and muscle support for athletes, comprising:
   (a) an elastic compression short having means for conforming said compression short tightly to the pelvis, groin area, and lower abdominal muscles of the user, a waistband, and leg portions designed to extend at least partially down the thigh of the wearer for applying graduated compressive forces to the hamstring and groin area muscles of the wearer;
   (b) an elastic support strap having means for engaging the spine from approximately the sacrum to at least the $L_3$ lumbar vertebrae operatively connected to and restrained from vertical movement by the compression short and designed to circumferentially extend around the waist area of the wearer;
   (c) stay means sized to supportively span that area of the wearer's back extending between the sacrum and at least three vertebrae of the wearer's lumbar spine;
   (d) means operatively connected with said support strap for aligning said stay means adjacent the spine of the wearer such that said stay means extend along the wearer's back from the sacrum to at least three vertebrae of the wearer's lumbar spine;
   (e) means operatively connected with said stay means for urging said stay means toward the wearer's back thereby partially immobilizing movement of two or more lumbar vertebrae of the wearer's spine; and
   (f) wherein the above combination maintains the lumbar vertebrae of the wearer in a predetermined anatomical relationship relative to one another regardless of the degree of movement activity of the wearer.

* * * * *